United States Patent [19]

Valentini et al.

[11] Patent Number: 4,787,429
[45] Date of Patent: Nov. 29, 1988

[54] DEVICE FOR COUPLING A SMALL TUBE TO AN APPARATUS ADAPTED FOR FITTING A SYRINGE TO A DRUG HOLDING BOTTLE

[75] Inventors: Luigi Valentini, Milan; Mario Coccia, Cesano Boscone, both of Italy

[73] Assignee: Farmitalia Carlo Erba S.p.A., Milan, Italy

[21] Appl. No.: 75,776

[22] Filed: Jul. 20, 1987

[30] Foreign Application Priority Data

Jul. 25, 1986 [IT] Italy ............................ 22647/86[U]

[51] Int. Cl.$^4$ ......................... B65B 3/04; A61M 5/00
[52] U.S. Cl. .................................. 141/383; 141/382; 141/329; 604/411; 604/415; 285/921
[58] Field of Search .................... 141/24–28, 141/311, 312, 319, 329, 330, 346, 368, 369, 370, 371, 372, 375, 382, 383, 384, 385, 386; 285/921, 319, 320, 423; 604/403, 407, 411, 414, 415, 905, 201, 240, 243

[56] References Cited

U.S. PATENT DOCUMENTS

| | | | |
|---|---|---|---|
| 1,315,484 | 9/1919 | Fesler | 141/383 X |
| 3,368,592 | 2/1968 | Thiel et al. | 141/383 X |
| 3,486,539 | 12/1969 | Jacuzzi | 141/329 |
| 3,486,730 | 12/1969 | Potash | 141/346 X |
| 3,542,240 | 11/1970 | Solowey | 604/415 X |
| 3,682,315 | 8/1972 | Haller | 604/415 X |
| 4,089,432 | 5/1978 | Crankshaw et al. | 604/415 X |
| 4,182,388 | 1/1980 | Sellen | 141/384 X |
| 4,203,443 | 5/1980 | Genese | 141/329 X |
| 4,269,237 | 5/1981 | Berger | 141/346 |
| 4,291,701 | 9/1981 | Browman | 128/675 |
| 4,312,349 | 1/1982 | Cohen | 604/415 X |
| 4,326,569 | 4/1982 | Vaillancourt | 141/383 |
| 4,369,781 | 1/1983 | Gilson et al. | 604/403 |
| 4,451,069 | 5/1984 | Melone | 285/921 X |
| 4,507,113 | 3/1985 | Dunlap | 604/411 X |
| 4,523,780 | 6/1985 | Cheer | 285/921 X |
| 4,564,054 | 1/1986 | Gustavsson | 141/329 |
| 4,576,211 | 3/1986 | Valentini et al. | 141/329 |
| 4,675,020 | 6/1987 | McPhee | 604/411 |

*Primary Examiner*—Henry J. Recla
*Assistant Examiner*—Ernest G. Cusick
*Attorney, Agent, or Firm*—Oblon, Fisher, Spivak, McClelland & Maier

[57] ABSTRACT

Device for easily and simply coupling to the free end of a small tube (7) mounted on a transfusion needle an apparatus of the type used for coupling a syringe to a drug holding bottle. The device comprises a hollow shaped body (1) that can be coupled to the small tube (7). An axial passageway (13) in the body (1) is closed by a plug (5). A collar (2) shaped as the mouth of a conventional drug bottle projects from the body (1). The collar (2) extends axially and a continuous annular recess (3) is formed therein. The recess (3) has a profile and arrangement sized and shaped to allow for the teeth projecting from the resilient lugs of the apparatus to which the device is to be coupled to be inserted and locked therein.

5 Claims, 1 Drawing Sheet

DEVICE FOR COUPLING A SMALL TUBE TO AN APPARATUS ADAPTED FOR FITTING A SYRINGE TO A DRUG HOLDING BOTTLE

BACKGROUND OF THE INVENTION

U.S. patent application Ser. No. 06/879,886, filed June 30, 1986 discloses a device for coupling, under safe conditions, one end of a drug delivering small tube to an apparatus for coupling a syringe to the drug holding bottle. This device has a free end (that is, its end which is to be coupled to the mentioned apparatus) which has substantially the form of a body shaped as the mouth of a conventional bottle of the type used for holding a drug. From the shaped body three or more longitudinal fins project. The fins have an even flat longitudinal outer profile and operate for assuring an axial insertion of the above-mentioned free end of the device and a firm holding of the device in the seat of the apparatus whereon the drug holding syringe is mounted.

As stated in the above mentioned patent application, the apparatus to be coupled to the syringe is provided with three or more resilient lugs each of which bears a tooth which, as the free end of the device is inserted into the apparatus seat, engages under the free edge of the device. Such an apparatus is disclosed in U.S. Pat. No. 4,576,211.

It has been found that the provision of the longitudinal fins projecting from the body (and the radially outermost longitudinal peripheral edge of which is even) may cause latching problems if the longitudinal fins are arranged in front of the teeth of the flexible or resilient lugs of the apparatus. In fact, if the device is not arranged with its fins disengaged from the resilient lug teeth of the apparatus, then the device can not be coupled to the apparatus. Moreover, the user may not notice the drawback, with the very dangerous consequence (it should be remembered that many drugs are very toxic) that the device may detach from the apparatus during the drug delivering step.

OBJECT OF THE INVENTION

Thus, the main object of the present invention is to provide a device of the mentioned type which may be easily inserted into the seat of the mentioned apparatus, while holding always a longitudinal orientation during the insertion, and being always firmly held in the seat, in an oscillation free condition, and being firmly engaged by the teeth projecting from the flexible or resilient lugs of the apparatus, as soon as the device is introduced into the seat.

SUMMARY OF THE INVENTION

This device comprises a shaped body defining a hollow open at a first end whereat a lug is formed for coupling the device to a small discharging tube. The device is also open at a second end whereat a hollow closure resilient plug is provided. The body is at the plug, with a projecting collar the shape and size of which, in a plane perpendicular to the longitudinal axis of the shaped body, are analogous to or like those of a conventional bottle of the type used for holding drugs. The collar axially peripherally extends for a length greater than that of the collar of a conventional bottle so as to define an elongated cylindrical surface. A continuous annular recess is formed in the elongated cylindrical surface, and the recess is designed and arranged so as to allow for the teeth projecting from the resilient lugs of the apparatus to which the device is to be coupled to be inserted thereinto and locked therein.

BRIEF DESCRIPTION OF THE DRAWINGS

In order to better understand the structure and characteristics of the subject device, a preferred embodiment thereof will be disclosed hereinafter, with reference to the accompanying drawing.

DESCRIPTION OF THE PREFERRED EMBODIMENT

Figure 2:
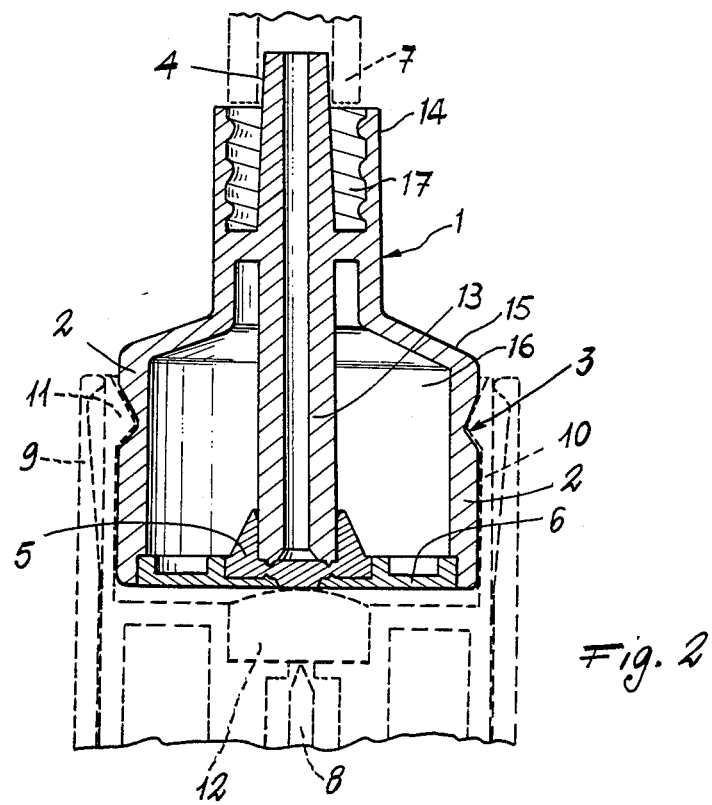
FIG. 2 is an enlarged scale cross-sectional view of the device.
Figure 1:
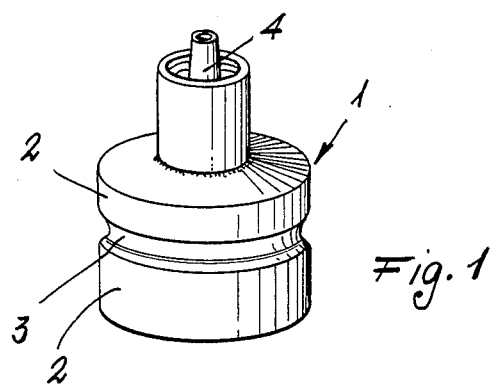
FIG. 1 is a perspective view of a device according to the present invention.

The device shown in the drawings comprises a shaped body 1 which is laterally delimited by a first cylindrical wall 2 on the outer surface of which there is formed an annular recess 3, a second cylindrical wall 14 that is coaxial to the first cylindrical wall 2, and a conical wall 15 that joins the first cylindrical wall 2 to the second cylindrical wall 14 and that is also coaxial to the first cylindrical wall 2. Inside the cylindrical wall 2 and along its axis, a lug 4 extends. An axial passageway 13 extends the length of the shaped body 1 inside the lug 4. The axial is open at the top end thereof (as shown in the drawings). At the other end of the shaped body 1, the axial passageway 13 is closed by a resilient plug 5 (made of rubber or like material) which is held firmly pressed on the lower end of the lug 4 by means of a small rigid holding disc 6 affixed to the cylindrical wall 2.

The lower end of the body 1 comprises the previously mentioned first cylindrical wall 2, which is concentric to the longitudinal axis of the shaped body 1; a first blind recess 16 that is within the first cylindrical wall 2, that is concentric to the longitudinal axis of the shaped body 1, and that is open to the lower end of the shaped body 1; and the previously mentioned lug 4, the lower end of which is at least substantially cylindrical, the radially outer surface of which defines one side of the first blind recess 16, which is concentric to the longitudinal axis of the shaped body 1, and which contains the axial passageway 13. The upper end of the body 1 comprises the previous mentioned second cylindrical wall 14, which is concentric to the longitudinal axis of the shaped body 1; a second blind recess 17 that is within the second cylindrical wall 14, that is concentric to the longitudinal axis of the shaped body 1, and that is open to the upper end of the shaped body 1; and the previously mentioned lug 4, the upper end of which is at least substantially conical, the radially outer surface of which defines one side of the second blind recess 17, which is concentric to the longitudinal axis of the shaped body 1, and which contains the axial passageway 13.

On the free projecting end of the lug 4 there can be mounted one end of a resilient small tube 7 (a portion of which has been shown by a dashed line in FIG. 2). To the other end of the resilient small tube 7 an epicranial needle may be coupled for the transfusion into a vein of a patient of a drug which is injected into the axial passageway 13 by a needle 8 (which is shown in phantom in FIG. 2) mounted on a (not shown) syringe.

The needle 8 is included in an apparatus like that disclosed in U.S. Pat. No. 4,576,211. At the lower portion of FIG. 2 there is shown, by a dashed line, the end portion of this apparatus whereat a seat is formed for housing and holding the device according to the present invention.

It should briefly be remembered that this seat is defined by a tubular cylindrical wall 9 within which resilient lugs 10 extend, a tooth 11 projecting inwardly from each resilient lug 10.

At the center of the apparatus seat, a rubber or the like pad 12 projects. As the subject device is locked in the seat, as is schematically shown in FIG. 2, the pad 12 is held firmly pressed against the resilient plug 5.

The operation of the needle 8 bearing apparatus to which the subject device may be coupled will be not disclosed herein, since it has been clearly illustrated in the above mentioned U.S. Pat. No. 4,576,211.

A main feature of the device according to the present invention is that the cylindrical wall 2 has a cross-section equal or analogous to the cross-section of the collar of a conventional drug holding bottle. The above mentioned cylindrical wall 2 extends axially for a length greater than the depth of the housing seat defined by the cylindrical wall 9 and the resilient lugs 10 of the apparatus, as is clearly shown in FIG. 2. Finally, and that the annular recess 3 is arranged and shaped so that, as the device is coupled to the apparatus, the teeth 11 of the resilient lugs 10 will always enter the annular recess 3 to be locked therein. This means that, as soon as the device is inserted into the seat of the apparatus and the resilient plug 5 is pressed against the pad 12, the teeth 11 will enter the annular recess 3, thereby always firmly engaging the device with the apparatus.

The fact that the cylindrical wall 2 extends axially in the indicated way is also an essential feature, since in this way a great resting area is provided for the outer surface of the cylindrical wall 2 against the adjoining surface of the apparatus seat. For this reason, the device forms a nearly rigid body with respect to the apparatus, since it can not oscillate in the apparatus housing seat.

We claim:

1. A device for coupling a tube to an apparatus for coupling a syringe to a drug holding bottle, said device comprising:
    (a) a body having a first end, a second end, a longitudinal axis, and an axial passageway extending from said first end of said body to said second end of said body, said first end of said body being adapted to be connected to a hollow tube such that said axial passageway is in fluid communication with the interior of said hollow tube, said body comprising a first at least substantially cylindrical wall at said second end of said body that is concentric to said longitudinal axis and that has an external annular recess therein spaced from said second end of said body, and
    (b) a resilient plug mounted on said second end of said body so as to close said axial passageway;
    (c) said second end of said body comprising:
        (i) said first at least substantially cylindrical wall;
        (ii) a first blind recess that is within said first cylindrical wall, that is concentric to said longitudinal axis, and that is open to said second end of said body; and
        (iii) a lug the radially outer surface of which defines one side of said blind first recess, which is concentric to said longitudinal axis, and which contains said axial passageway, the radially outer surface of said lug which defines one side of said first blind recess being at least substantially cylindrical.

2. A device as recited in claim 1 wherein said first end of said body comprises:
    (a) a second at least substantially cylindrical wall concentric to said longitudinal axis;
    (b) a second blind recess that is within said second at least substantially cylindrical wall, that is concentric to said longitudinal axis, and that is open to said first end of said body; and
    (c) said lug, the radially outer surface of which defines one side of said second blind recess, which is concentric to said longitudinal axis, which extends axially beyond said second at least substantially cylindrical wall, which contains said axial passageway, and which decreases in diameter towards said first end of said body.

3. A device as recited in claim 2 wherein the radially inner surface of said second blind recess is threaded.

4. A device as recited in claim 2 wherein the radially outer surface of said lug which defines one side of said second blind recess is at least substantially conical.

5. A device as recited in claim 1 and further comprising a rigid disk:
    (a) mounted on said first at least substantially cylindrical wall and said lug;
    (b) mounting said resilient plug; and
    (c) closing said first blind recess.

* * * * *